United States Patent [19]

Schneider et al.

[11] 4,033,799

[45] July 5, 1977

[54] IONIC HYDROGENOLYSIS OF BINOR-S FOR USE AS A HIGH ENERGY FUEL

[75] Inventors: Abraham Schneider, Overbrook Hills; Edward J. Janoski, Havertown, both of Pa.

[73] Assignee: Sun Ventures, Inc., St. Davids, Pa.

[22] Filed: May 16, 1975

[21] Appl. No.: 578,070

[52] U.S. Cl. .............................. 149/120; 149/109.4; 260/666 PY; 260/690; 252/477 Q
[51] Int. Cl.$^2$ .................. C06B 23/00; B01J 35/00; C07C 1/00
[58] Field of Search ........ 260/666 R, 666 PY, 690; 252/477 Q, 443, 447, 472; 149/109.4, 120

[56] References Cited

UNITED STATES PATENTS

| | | | |
|---|---|---|---|
| 3,258,502 | 6/1966 | Cannell | 260/666 PY |
| 3,265,749 | 8/1966 | Cannell | 260/666 PY |
| 3,282,663 | 11/1966 | Muller | 260/666 PY |
| 3,326,992 | 6/1967 | Muller | 260/666 PY |
| 3,326,993 | 6/1967 | Bastian | 260/666 PY |
| 3,544,485 | 12/1970 | Taira | 260/690 |

OTHER PUBLICATIONS

Schrauzer, et al., Journal of the American Chemical Society, 88:21, Nov. 5, 1966, pp. 4890–4894.

*Primary Examiner*—Samuel W. Engle
*Assistant Examiner*—Donald P. Walsh
*Attorney, Agent, or Firm*—Donald R. Johnson; J. Edward Hess; Anthony Potts, Jr.

[57] ABSTRACT

Ionic hydrogenolysis of Binor-S, a $C_{14}$ heptacyclic saturated hydrocarbon, yields a low melting point product containing predominantly hexacyclics and lesser amounts of pentacyclics. Hydrogenolysis occurs at about 50°–200° C and at about 100–10,000 p.s.i.g. in the presence of a palladium-on-carbon catalyst, palladium-on-alumina or Raney nickel and is promoted by a hydrogen halide or its equivalent. Resulting product has utility as a high energy fuel.

15 Claims, No Drawings

IONIC HYDROGENOLYSIS OF BINOR-S FOR USE AS A HIGH ENERGY FUEL

CROSS REFERENCE TO RELATED APPLICATION

This application is related to U.S. application Ser. No. 578,308, filed same date by same inventors. Subject matter of this related application is the preparation of novel alkyl ethers of Binor-S.

BACKGROUND OF THE INVENTION

The invention herein described was made in the course of or under a contract thereunder with the United States Air Force Systems Command.

This invention relates to mixtures resulting from the hydrogenolysis of "Binor-S". More particularly the invention relates to mixtures of hexacyclics and pentacyclics and other compounds resulting from the hydrogenolysis of Binor-S, a $C_{14}$ heptacyclic saturated hydrocarbon.

It is an object of present invention to provide novel compositions of hexacyclics and pentacyclics and other compounds which compositions are characterized by low freezing points, low melting points and be relatively high net heats of combustion. Said compositions have utility as a high energy fuel which can be used in either jet or rocket propulsion. Jet propulsion includes a jet engine which can be used for a missile plane and others and includes the three basic types, i.e., ramjet, turbo-jet and pulse jet. The term jet generally refers to a device requiring air whereas rocket generally refers to a device containing its own oxygen.

It is also an object of present invention to provide a novel method for preparing the foregoing novel compositions. It is also an object to provide a controlled reaction so that the amount of various components of the novel composition can be varied substantially. Another object is the hydrogenolysis of Binor-S at high conversions (>95 percent).

Preparation of Binor-S is disclosed in JOURNAL OF THE AMERICAN CHEMICAL SOCIETY, 88:21, November 5, 1966, pages 4890-4894, title of article "$\pi$ Complex Multicenter Reactions Promoted by Binuclear Catalyst Systems". "Binor-S a New Heptacyclotetradecane via Stereospecific Dimerization of Bicycloheptadiene", by G. N. Schrauzer, B. N. Bastian and G. A. Fosselius. Same article also discloses hydrogenation of Binor-S over Pt at 200° C and 4600 p.s.i. Products of the hydrogenation are reported as $C_{14}H_{20}$ (94 percent) and $C_{14}H_{18}$ (6 percent). Binor-S is known by its chemical name of endo,cis,endo-heptacyclo [5.3.1.1$^{2,6}$.1$^{4,12}$.1$^{9,11}$.0$^{3,5}$.0$^{8,10}$]tetradecane. It's melting point is about 65° C. Binor-S can be depicted by the following structural formula:

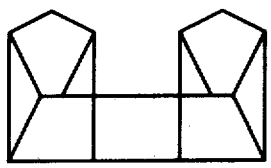

Binor-S is a $C_{14}H_{16}$ hydrocarbon containing seven rings and a C/H atomic ratio of 0.875.

Preparation of dimers of bicycloheptadiene is disclosed in U.S. Pat. No. 3,326,993 issued June 20, 1967. The latter discloses that a mixture of bicycloheptadiene dimers has utility as high energy fuel.

Hydrogenation of the foregoing bicycloheptadiene dimers improves its stability towards autoxidation thereby enhancing its utility as a fuel. Such hydrogenated dimers of bicyloheptadiene, in which crystallization has been produced by maintaining at −110° F. (−78.9° C.), are completely melted only by warming to +25° F. (−3.9° C.). The rather high melting point of the last crystalline material of said dimer can hinder its fluid flow at low ambient temperatures.

In contrast, applicants' product, which has been induced to crystallize by maintaining for a prolonged period at −110° F. (78.9° C.), is completely melted on warming to −45° F. (−42.8° C.).

SUMMARY OF THE INVENTION

Binor-S is hydrogenolyzed using palladium-on-carbon, palladium-on-alumina or Raney nickel catalyst promoted by a hydrogen halide or its equivalent. Temperature of the hydrogenolysis is about 50°–200° C. and the pressure is about 100°–10,000 p.s.i.g. Suitable solvents may also be used. Resulting product contains, in addition to any unreacted starting material, larger amounts of hexacyclics and lesser amounts of pentacyclics and other compounds. Notwithstanding the latter, the ionic hydrogenolysis can be controlled so that the resulting product can contain essentially hexacyclics. A resulting mixture can have a density of about 1.08, a net heat of combustion of about 160,000 BTU and a melting point of the last crystalline material of about −45° F (−42.8° C.).

DESCRIPTION

The method of the hydrogenolysis of Binor-S so that desired components are obtained depends on the presence of a promoter containing a halide. The promoter can be a hydrogen-halide, e.g., hydrogen chloride, or it can be an organic halide, such as ethyl chloride, isopropyl iodide, n-amyl bromide, ethylidene bromide, fluorobenzene, p-chlorotoluene, cyclopentyl chloride, and the like. Alkylhalides such as cyclohexylbromide are preferred. An alkylhalide is favored because it is more easily handled than the corresponding hydrogen halide. Of the four halides, i.e., fluoride, chloride, bromide and iodide, bromide is preferred. When an alkylhalide is used cyclohexyl bromide, t-butyl chloride, isopropyl bromide or isopropylchloride are preferred. In the presence of hydrogen the palladium-on-carbon, palladium-on-alumina or Raney nickel cause the alkylhalide to form the corresponding saturated alkyl hydrocarbon and the hydrogen halide.

The amount of promoter containing halide present should be a promoting amount. While higher amounts accelerate the reaction rates, too much could be uneconomical. An operative range is about 0.0001–0.004 gram moles of equivalent hydrogen halide per gram of Binor-S, a preferred range is about 0.002–0.002. Equivalent hydrogen halide means either the amount of hydrogen halide used or that formed by the complete liberation of hydrogen halide from the organic halide.

The hydrogenolysis catalyst can be palladium-on-carbon (hereinafter Pd/a) or Raney nickel. Normally the Pd/C or Pd/a contains about 0.5–12 weight percent palladium with a higher percentage, e.g., 10% preferred. Generally the amount of catalyst is that amount which is effective to catalyze the reaction. Typical operative ranges include about 0.01–10 weight percent based on the amount of Binor-S to be treated. A preferred range of catalyst is about 0.5–5 weight percent.

The hydrogen used is free of sulfur or sulfur-containing compounds. Any other impurity in the hydrogen which adversely effects the reaction, catalyst or products should not be present.

A solvent can be used to reduce the viscosity of the Binor-S while it is undergoing hydrogenolysis. The solvent can be saturated hydrocarbon, and preferably an inexpensive one. It should also be easily separated from the reactant and products and non-reactive with the foregoing. The saturated hydrocarbon should be liquid at ambient temperatures, particularly suitable are the cycloalkyl hydrocarbons such as methylcyclohexane, ethylcyclohexane, dimethylcyclohexane, decalin and the like. If a solvent is used generally the amount can vary between about 2 to 50 volume percent based on the volume of Binor-S.

An alternative to the use of a solvent is to have the hydrogenolysis of the Binor-S occur at a temperature above its melting point. Also a combination of temperature and solvent could be used so that the viscosity of the resulting mixture permits ease of operation, e.g., mixing and/or pumping.

The temperature of the hydrogenolysis generally will be about between 50°–200° C. with 75°–150° C. a preferred temperature range. The pressure of the hydrogenolysis generally will be about 100–10,000 p.s.i.g. with 250–5000 p.s.i.g. a preferred pressure range.

The ionic hydrogenolysis of the Binor-S can be represented by the following formula reaction:

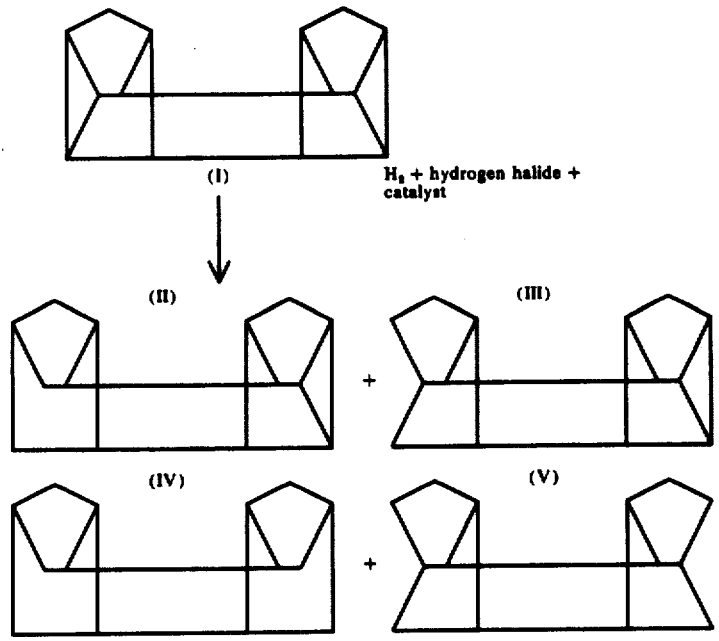

Compounds II and III are dihydro-Binor-S, both contain 6 rings, have a C/H atomic ratio = 0.778 and have an empirical formula of $C_{14}H_{18}$. Compounds IV and V are two of the four possible tetrahydro-Binor-S isomers, contain 5 rings, have a C/H atomic ratio = 0.700 and have an empirical formula of $C_{14}H_{20}$.

Hydrogenolysis according to present invention favors the formation of dihydro-Binor-S since most of the Binor-S disappears before the concentration of the pentacyclics, e.g., IV and V, increases dramatically in conjunction with a decrease in the concentration of the hexacyclics (II and III). Also this method favors the addition of hydrogen atoms of the carbon atoms that form the cyclopropane rings contained within Binor-S. Another result of present invention is that the product is a more complex mixture, i.e., it contains many different compounds.

The influence of the promoter upon conversion and selectivity is demonstrated by the following data obtained via similar runs:

| Conditions* | Weight % of Products & Reactant | | | |
|---|---|---|---|---|
| | Binor-S | Hexa-cyclics | Penta-cyclics | Other** |
| Without Promoter, after 20 hours | 48.2 | 27.5 | 21.9 | 2.4 |
| With Promoter, after 18 hours | 36.5 | 44.6 | 7.7 | 10.8 |

*Purified 14.1 g Binor-S, 100° C., 0.45 g of 10% Pd/C, 127 ml methylcyclohexane, 1000 p.s.i.g.
**Hydrocarbons having a boiling point lower than the pentacyclic.

The favored formation of the hexacyclics with the promoter present is believed to be caused by the addition, as an illustration, of the HBr to a cyclopropane ring. One of the functions of the Pd/C (also the Pd/a and Raney nickel) catalyst is to hydrogenolyze, e.g., the bromide from the hexacyclic bromide to form saturated hexacyclic products and hydrogen bromide. The newly released hydrogen bromide then adds to another cyclopropane ring to continue the process. Because the foregoing is believed to be a possible mechanism for the hydrogenolysis of Binor-S it is referred to as an "ionic hydrogenolysis". Examples of non-ionic hydrogenolysis are wherein the catalyst is either $PtO_2$ or rhodium-on-carbon (hereinafter Rh/C) while the feed, Binor-S, contains HBr or is completely deprived HBr. Under such conditions compounds III and V are favored. Another example of non-ionic hydrogenolysis is where the catalyst is Pd/C and no hydrogen halide is present.

Binor-S can be made by the dimerization of norbornadiene with the catalyst system CoBr$_2$(triphenylphosphine)$_2$-boron trifluoride etherate. Thus Binor-S, as prepared, may contain a trace of indigenous bromide from the CoBr$_2$. This indigenous halide may be sufficient to cause ionic hydrogenation. Binor-S which is carefully treated to remove any indigenous halide and then treated with hydrogen (without promoter) forms substantially different products than that obtained via ionic hydrogenolysis.

The amount of promoter present can have an appreciable impact on the conversions and selectivity. This is demonstrated by the following data obtained vis similar runs:

| | | Weight % | | |
|---|---|---|---|---|
| Conditions* | Binor-S | Hexa-cyclics | Penta-cyclics | Others |
| With 0.0188 wt.% of added equivalent HBr; after 12¼ hours | 47.5 | 39.2 | 1.2+ | 8.6+ |
| With 0.1811 wt.% of added equivalent HBr; after 8¼ hours | 4.8 | 17.4 | 46.7 | 31.3 |

*Purified 14.1 g Binor-S, 100° C., 0.45 g 10% Pd/C, 127 ml methylcyclohexane, 1000 p.s.i.g., .0188 wt.% of HBr equals 0.00023 moles per gram of Binor-S.

As can be seen the use of almost 10 times the amount of promoter a accelerates the reaction rate. Thus the conversion of Binor-S is accelerated as well as the conversion of hexacyclics and pentacyclics. The others are low boiling constituents. Therefore, the composition of the final product can be controlled by the amount of promoter present.

As noted heretofore the resulting mixture prepared by ionic hydrogenolysis of Binor-S has a melting point property, in addition to a viscosity, density and heating value, which enables it to be used as a high energy fuel. High energy fuel refers to a fuel that is to be used in volume-limited applications and therefore should contain a relatively large amount of BTU's per gallon. Such fuels are highly desirable in certain types of jet propulsion such as in missiles. Such fuels may also have application in volume-limited rockets. The foregoing devices are used in airplanes, boats, missiles, space vehicles, weapons and others. In all of these uses, the ambient temperature can vary from a high 120° F of a desert to the below freezing temperature of space or an arctic region. Thus in some instances the melting point of the last crystalline material in the resulting mixture can be less than 10° C and the mixture is satisfactory for use as a fuel. In other instances the melting point should be less than 0° C or even less than −20° C.

Influencing the melting point of the last crystal of applicants' resulting mixture is the amount of unreacted, high-melting Binor-S contained therein. As the required melting point decreases the amount of unreacted Binor-S that can be present decreases. Unwanted unreacted Binor-S can be removed by fractional crystallization for example, or other known techniques. Also the amount of unreacted Binor-S remaining can depend on whether or not the fuel is heated to avoid fluid flow problems caused by ambient freezing temperatures.

The following examples and comparative work serve to further illustrate applicant's invention; also describes how the starting material, i.e., Binor-S was prepared.

EXAMPLES

Preparation of Binor-S

Norbornadiene(bicyclo[2.2.1]hepta-2,5-diene) was dimerized with the catalyst system CoBr$_2$(triphenylphosphine)$_2$-boron trifluoride etherate. The structure of the diene is as follows:

Afterwards methylene chloride was used to dissolve the organic phase of the reaction mixture and to separate the latter from the inorganic phase of catalyst components. Then the methylene chloride solution was washed with potassium carbonate to neutralize any free halogen acid and dried with the use of a drying agent such as anhydrous sodium sulfate. Upon cooling the treated methylene chloride solution, Binor-S crystallized. The crystals were filtered from the liquid and then vacuum distilled to give solid Binor-S which had a grayish tinge. The foregoing procedure has been described in the literature.

The foregoing preparation procedure gives what shall be referred to as a "crude" Binor-S.

To prepare a "pure" Binor-S the mixture resulting from the dimerization of norbornadiene was dissolved in pentane. The resulting solution was washed with aqueous potassium carbonate and then dried as above. Upon cooling the Binor-S crystallized. The filtered crystals were vacuum distilled and the distilled Binor-S was recrystallized from acetone and redistilled under vacuum. The resulting "purified" Binor-S was colorless in contrast to the grayish tinged "crude" Binor-S.

Hydrogenolysis of Binor-S

Generally, the following examples were conducted at 100° C. and 1000 psig pressure in a high pressure, rocking type reactor of 0.3 liter capacity. Charges of 150 milliliter were used. The concentration of Binor-S in the solvent, in this case methylcyclohexane, was 14.4 weight percent. With the exception of Run 3 the solution of Binor-S and methylcyclohexane prior to hydrogenolysis was percolated through basic Woelm alumina (grade 1) to remove any trace of the catalyst component CoBr$_2$(triphenylphosphine)$_2$ which remained dissolved in the Binor-S. The amount of catalyst, i.e., 10 percent Pd/C, was as shown on the accompanying tables. During the hydrogenolysis periodic monitoring of the contents of the reaction was carried out by withdrawing small samples from the liquid phase through a vent tube in the reactor. The samples were analyzed by high-efficiency capillary vapor phase chromatography with electronic integration of the data. The yields are reported as peaks.

Results of the hydrogenolysis of crude Binor-S are shown in Table I (Run 1). The data indicates almost 100 percent conversion of Binor-S after about 27 hours. As the reaction proceeded the amount of low boiling products continued to increase. The amount of hexacyclic saturated product increased until about 7-12 hours have lapsed and then its quantity decreased. The amount of pentacyclic saturates continued to increase throughout the 27 hours.

Run 1 was generally repeated, however, a temperature of 50° C. was used. No hydrogenolysis occurred at this low temperature. By comparison at 100° C. the hydrogenolysis would be called slow but steady.

The product from the 27.25 hour test of Run 1 had the following properties:

| | |
|---|---|
| Melting point of the last crystal, ° F. | <−45 |
| Density, 20/4° C. | 1.0829 |
| Viscosity centistokes at 100° F. | 14.3 |
| Net Heating Value, BTU/gal | 161,762 |

Surprisingly, the hydrogenolysis of pure Binor-S, as shown in Table II (Run 2) gave different results. The production of minor products (low boiling) was minimized. Conversion of Binor-S was relatively slow. After 20 hours formation of pentacyclics product was almost as large as that of hexacyclic material even though almost half of the Binor-S was unconverted and selectivity for the hexacyclic product formed was poor.

Thus, comparison of conversion of Binor-S, and products formed over a period of time for Runs 1 and 2 suggests that bromide has a beneficial influence on the reaction product and reaction rates. This suggestion was confirmed by Runs 3, 4 and 5.

In Run 3 (Table III) a "purified" Binor-S containing a small amount of added equivalent hydrogen bromide was treated with hydrogen as in Runs 1 and 2. The results of Run 3 are listed in Table III. Conversion of Binor-S in Run 3 was slower than that in Run 1, but faster than the rate of conversion in Run 2. Product distribution in Run 3 resembled that in Run 1, but was significantly different from that obtained in Run 2.

To determine the influence of added equivalent hydrogen bromide Run 4 was made. In this hydrogenolysis the amount of cyclohexyl bromide was increased from 5 microliters for run 3 to 48 microliters. The results of this run are shown in Table IV. Comparison of conversion and products distribution of Runs 4 and 3 indicate that large amounts of equivalent HBr cause substantial changes. With a relatively large amount of equivalent HBr production of one hexacyclic saturate (peak b) was eliminated, and production of pentacyclics was substantially increased. A new peak (peak 2) showed up in the low boiling minor products. Rate of conversion of Binor-S was the fastest in Run 4.

The product from the 8.5 hour test of Run 4 had the following properties:

| | |
|---|---|
| Melting point of the last crystal, ° F. | 0 |
| Density, 20/4 | 1.0748 |
| Viscosity, centistokes at 100° F. | 15.5 |

To determine whether catalyst concentration might influence conversion and product distribution hydrogenolysis of purified Binor-S was made using a large concentration of Pd/C (5 wt. percent versus 3 wt. percent). Results of Run 5 are shown in Table V. Conversion of Binor-S to hexacyclic saturates appears to have peaked after 25 hours while production of low-boiling minor products was minimized.

The product from the 24.75 hour test of Run 5 had the following properties:

| | |
|---|---|
| Melting point of the last crystal, ° F. | −10 |
| Density, 20/4 | 1.0873 |

-continued

| | |
|---|---|
| Viscosity, centistokes at 100° F. | 12.8 |
| Net Heating Value, BTU/gal | 163,353 |

Comparative Runs

To compare the catalyst, i.e., Pd/C, used in the previously discussed Runs 1-5, Run 6 was made using rhodium-on-carbon (Rd/C) catalyst. Table VI contains the data obtained from Run 6. While this reaction was relatively slow, generally because of the lower reaction temperature (50° C.) and lower concentration of metal (5 percent versus 10 percent of Pd/C), a reaction did occur. This is in contrast to the previously reported unnumbered Run with Pd/C at 50° C. wherein no reaction occurred.

The product of Run 6 after 78 hours had the following physical properties:

| | |
|---|---|
| Melting point of the last crystal, ° F. | +25 |
| Density, 20/4 | 1.0841 |
| Viscosity, centistokes at 100° F. | 12.4 |

To compare yields, etc. with Pd/C or Rd/C catalyst, Run 7 was made using platinum-oxide (PtO$_2$). The Binor-S was dissolved in a suitable amount of acetic acid, and Adams catalyst was used in the amount of 0.4 grams PtO$_x$/0.1 mole of Binor-S. Temperature was ambient and the pressure was about 2–3 atmospheres of hydrogen. The results of Run 7 is shown in Table VII.

The data of Run 7 indicates that the product consisted mostly of hexacyclics and pentacyclics after a short period of time, but that after a somewhat longer period of time the forming of pentacyclics was favored. The hydrocarbon measured by the pentacyclic (C$_{14}$H$_{20}$) peak d probably has the following structure:

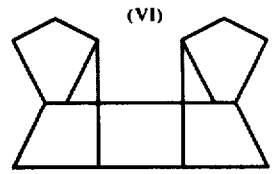

The hexacyclic (C$_{14}$H$_{18}$) peak b probably reflects the compound having the following structure:

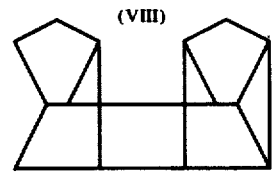

Other

Analogous results will be obtained using Raney nickel. Equally analogous results will be obtained using in place of the cyclohexylbromide other alkylhalides such as cyclohexylchloride, t-butyl chloride, isopropyl bromide or the hydrogen halides such as hydrogen chloride and hydrogen bromide. Use of solvents such as dimethylcyclohexane, ethylcyclohexane and decalin in place of methylcyclohexane will yield similar results.

TABLE I

RUN 1 — HYDROGENOLYSIS OF "CRUDE" BINOR-S WITH SMALL AMOUNT OF Pd/C

| Reaction Time,* hrs. | 1.25 | 3 | 5 | 7 | 9.5 | 12 | 15.5 | 27.25 |
|---|---|---|---|---|---|---|---|---|
| Binor-S | 63.4 | 44.7 | 35.1 | 26.0 | 16.6 | 11.1 | 4.1 | 0.01 |
| PRODUCTS | | | | | | | | |
| Low Boiling | | | | | | | | |
| Minor | 1.5 | 1.8 | 1.7 | 1.0 | 2.4 | 3.2 | 5.0 | 6.9 |
| Peak 1 | 2.9 | 4.1 | 5.0 | 6.0 | 6.7 | 7.1 | 7.7 | 8.1 |
| Peak 2 | 3.5 | 6.3 | 7.6 | 8.8 | 10.1 | 10.7 | 11.6 | 12.2 |
| TOTAL | 7.9 | 12.2 | 14.3 | 15.8 | 19.2 | 21.0 | 24.3 | 27.2 |
| Hexacyclic | | | | | | | | |
| Peak a | 20.6 | 30.9 | 34.2 | 38.4 | 42.0 | 44.2 | 41.7 | 34.2 |
| Peak b | 8.1 | 7.3 | 9.9 | 11.0 | 10.0 | 8.6 | 8.3 | 2.3 |
| TOTAL | 28.7 | 38.2 | 44.1 | 49.4 | 52.0 | 52.8 | 50.0 | 36.5 |
| Pentacyclic | | | | | | | | |
| Peak c | tr | 1.6 | 2.4 | 3.4 | 5.0 | 6.4 | 9.6 | 17.2 |
| Peak d | tr | 3.3 | 4.1 | 5.4 | 7.2 | 8.7 | 12.0 | 19.1 |
| TOTAL | tr | 4.9 | 6.5 | 8.8 | 12.2 | 15.1 | 21.6 | 36.3 |

*Other conditions; 14.1 g Binor-S 127 ml methylcyclohexane, 0.45 g 10% Pd/C
tr = trace

TABLE II

RUN 2 — HYDROGENOLYSIS OF "PURIFIED" BINOR WITH SMALL AMOUNT OF Pd/C

| Reaction Time,* hrs. | 2.5 | 7.5 | 11 | 20 |
|---|---|---|---|---|
| Binor-S | 88.3 | 66.6 | 61.7 | 48.2 |
| PRODUCTS | | | | |
| Low Boiling | | | | |
| Minor | 1.1 | 1.1 | — | 0.4 |
| Peak 1 | 0 | 0.7 | 0.6 | 0.9 |
| Peak 2 | 0 | 0.8 | 0.5 | 1.1 |
| TOTAL | 1.1 | 2.6 | 1.1 | 2.4 |
| Hexacyclic | | | | |
| Peak a | 2.3 | 5.4 | 6.5 | 8.8 |
| Peak b | 6.8 | 15.5 | 17.7 | 18.7 |
| TOTAL | 9.1 | 20.9 | 24.2 | 27.5 |
| Pentacyclic | | | | |
| Peak c | 0 | 0.3 | — | 0.9 |
| Peak d | 1.5 | 9.6 | — | 21.0 |
| TOTAL | 1.5 | 9.9 | 13.0 | 21.9 |

*Other conditions; 14.1 g Binor-S, 127 ml methylcyclohexane, 0.45 g 10% Pd/C

TABLE III

RUN 3 — HYDROGENOLYSIS OF "PURIFIED" BINOR-S CONTAINING SMALL AMOUNT OF ADDED BROMIDE AND SMALL AMOUNT OF Pd/C

| Reaction Time,* hrs | 3 | 12.25 | 18 | 23 | 33 | 39.25 | 56.5 | 72.75 |
|---|---|---|---|---|---|---|---|---|
| Binor-S | 76.0 | 47.5 | 36.5 | 26.8 | 15.3 | 13.0 | 7.3 | 3.4 |
| PRODUCTS | | | | | | | | |
| Low Boiling | | | | | | | | |
| Minor | 0.8 | tr | 0.1 | 0.3 | 0.9 | 0.6 | 1.0 | 1.6 |
| Peak 1 | 1.4 | 3.5 | 4.4 | 5.0 | 5.9 | 6.1 | 6.5 | 6.9 |
| Peak 2 | 2.1 | 5.1 | 6.3 | 7.3 | 8.5 | 8.7 | 9.4 | 9.7 |
| TOTAL | 4.3 | 8.6 | 10.8 | 12.6 | 15.3 | 15.4 | 16.9 | 18.2 |
| Hexacyclic | | | | | | | | |
| Peak a | 11.0 | 25.6 | 30.4 | 35.4 | 39.6 | 40.4 | 40.1 | 39.0 |
| Peak b | 7.5 | 13.6 | 14.6 | 14.1 | 13.0 | 12.3 | 10.8 | 7.8 |
| TOTAL | 18.5 | 39.2 | 45.0 | 49.5 | 52.6 | 52.7 | 50.9 | 46.8 |
| Pentacyclic | | | | | | | | |
| Peak c | tr | 1.3 | 2.2 | 3.5 | 5.6 | 6.6 | 8.9 | 11.5 |
| Peak d | 1.2 | 3.4 | 5.5 | 7.7 | 11.2 | 12.4 | 16.0 | 20.1 |
| TOTAL | 1.2 | 4.7 | 7.7 | 11.2 | 16.8 | 19.0 | 24.9 | 31.6 |

*Other conditions; 14.1 g Binor-S, 5 microliters cyclohexyl bromide, 127 ml methylcyclohexane, 0.45 g 10% Pd/C

TABLE IV

RUN 4 — HYDROGENOLYSIS OF "PURIFIED" BINOR-S CONTAINING LARGE AMOUNT OF ADDED BROMIDE AND SMALL AMOUNT OF Pd/C

| Reaction Time,* hrs | 1.75 | 8.5 |
|---|---|---|
| Binor-S | 74.5 | 4.8 |
| PRODUCTS | | |
| Low Boiling | | |
| Minor | 0.7 | 5.6 |
| Peak α | 0.0 | 7.1 |
| Peak 1 | 2.3 | 6.7 |
| Peak 2 | 2.8 | 11.9 |
| TOTAL | 5.8 | 31.3 |
| Hexacyclic | | |
| Peak a | 18.2 | 17.4 |
| Peak b | 0 | 0 |
| TOTAL | 18.2 | 17.4 |
| Pentacyclic | | |
| Peak c | 0 | 23.4 |
| Peak d | 0 | 23.3 |
| TOTAL | 0 | 46.7 |

*Other conditions; 14.1 g Binor-S; 48 microliters cyclohexyl bromide, 127 ml methylcyclohexane; 0.45 g 10% Pd/C

TABLE V

RUN 5 — HYDROGENOLYSIS OF "PURIFIED" BINOR-S WITH LARGE AMOUNT OF Pd/C

| Reaction Time,* hrs | 14.5 | 24.75 |
|---|---|---|
| Binor-S | 30.1 | 15.6 |
| PRODUCTS | | |
| Low Boiling | | |
| Minor | 0.3 | 0.8 |
| Peak 1 | 2.2 | 2.7 |
| Peak 2 | 3.0 | 3.5 |
| TOTAL | 5.5 | 7.0 |
| Hexacyclic | | |
| Peak a | 15.2 | 17.6 |
| Peak b | 18.3 | 12.5 |
| TOTAL | 33.5 | 30.1 |
| Pentacyclic | | |
| Peak c | 2.5 | 4.8 |
| Peak d | 28.4 | 42.5 |
| TOTAL | 30.9 | 47.3 |

*Other conditions; 50 g Binor-S; 50 ml methylcyclohexane, 2.7 g 10% Pd/C (5.3 wt %)

TABLE VI

RUN 6-HYDROGENOLYSIS OF "CRUDE" BINOR-S WITH Rd/C

| Reaction Time,* hrs | 48** | 78 |
|---|---|---|
| Binor-S | 24.2 | 15.3 |
| PRODUCTS | | |
| Low Boiling | | |
| Minor | 0.16 | 1.9 |
| Peak 1 | — | — |
| Peak 2 | — | — |

TABLE VI-continued

RUN 6-HYDROGENOLYSIS OF "CRUDE"BINOR-S WITH Rd/C

| | | |
|---|---|---|
| TOTAL | 0.16 | 1.9 |
| Hexacyclic | | |
| Peak a | 3.4 | 2.8 |
| Peak b | 20.6 | 16.8 |
| TOTAL | 24.0 | 19.6 |
| Pentacyclic | | |
| Peak c | tr | tr |
| Peak d | 50.2 | 63.2 |
| TITAL | 50.2 | 63.2 |

* Other conditions; 14.1 g Binor-S, 127 ml methylcyclohexane, 0.45 g 5% Rh/C, Reaction temperature 50° C
** 1.44% unaccounted

TABLE VII

RUN 7 — HYDROGENOLYSIS OF BINOR-S WITH PtO$_2$ — ACIDIC ACID SOLVENT

| Reaction Time,* hrs | 2 | 4 |
|---|---|---|
| Binor-S | 52.9 | 11.3 |
| PRODUCTS | | |
| Hexacyclic | | |
| Peak a | 4.6 | 5.1 |
| Peak b | 20.3 | 7.9 |
| TOTAL | 24.9 | 13.0 |
| Pentacyclic | | |
| Peak c | small | small |
| Peak d | 22.3 | 75.6 |
| TOTAL | 22.3+ | 75.6+ |

*Other conditions; ambient temperature, 2-3 atmospheres of H$_2$, 0.4 g PtO$_2$/0.1 mole of Binor-S

The invention claimed is:

1. A method for the ionic hydrogenolysis of Binor-S comprising:
contacting Binor-S with hydrogen in the presence of a promoting amount of a promoter selected from the group consisting of hydrogen halide and an organic halide and an effective amount of a catalyst selected from the following group: palladium-on-carbon, palladium-on-alumina and Raney nickel; said contacting occurring at a temperature of about 50°–200° C. and at a pressure of about 100–10,000 p.s.i.g.,
whereby the low melting point of the last crystalline material in the resulting mixture enables said mixture to be used as a high energy fuel at a low temperature.

2. Method according to claim 1 wherein the melting point enables the resulting mixture to be used in jet or rocket propulsion.

3. Method according to claim 2 wherein the melting point is less than 10° C.

4. Method according to claim 2 wherein the melting point is less than 0° C.

5. Method according to claim 2 wherein the melting point is less than −20° C.

6. Method according to claim 1 wherein the contacting temperature is about 75°–150° C.

7. Method according to claim 6 wherein the contacting pressure is about 250–5000 p.s.i.g.

8. Method according to claim 1 wherein the amount of promoter containing halide is about 0.0001–0.004 gram moles of equivalent hydrogen halide.

9. Method according to claim 1 wherein the amount of catalyst present is about 0.01–10 weight percent based on the amount of Binor-S.

10. Method according to claim 8 wherein the amount of catalyst present is about 0.01–10 weight percent based on the amount of Binor-S, the promoter containing halide is hydrogen bromide, the temperature is about 75°–150° C, the pressure is about 250–5000 p.s.i.g. and the melting point of the resulting mixture enables it to be used as a fuel for jet or rocket propulsion.

11. Method according to claim 1 wherein the amount of catalyst present is about 0.01–10 weight percent based on the amount of Binor-S and the organic halide is an alkyl halide present in the amount of about 0.0001–0.004 gram moles of equivalent hydrogen halide per gram of Binor-S, the temperature is about 75°–150° C, the pressure is about 250–5000 p.s.i.g. and the melting point of the resulting mixture enables it to be used as a fuel for jet or rocket propulsion.

12. A composition useful as a high energy fuel comprising a low melting point mixture of dihydro-Binor-S and tetrahydro-Binor-S, said mixture having at least 30 percent by weight of dihydro-Binor-S.

13. A composition according to claim 12 wherein the melting point of the last crystalline material in a mixture is less than 10° C.

14. A composition according to claim 13, wherein the mixture has at least 40 percent by weight of dihydro-Binor-S and the melting point is less than −20° C.

15. A composition according to claim 12 wherein the mixture has a density of about 1.08, a net heat of combustion of about 160,000 BTU/gallon, and a metling point of the last crystalline material is about −43° C.

* * * * *